Figure 1:
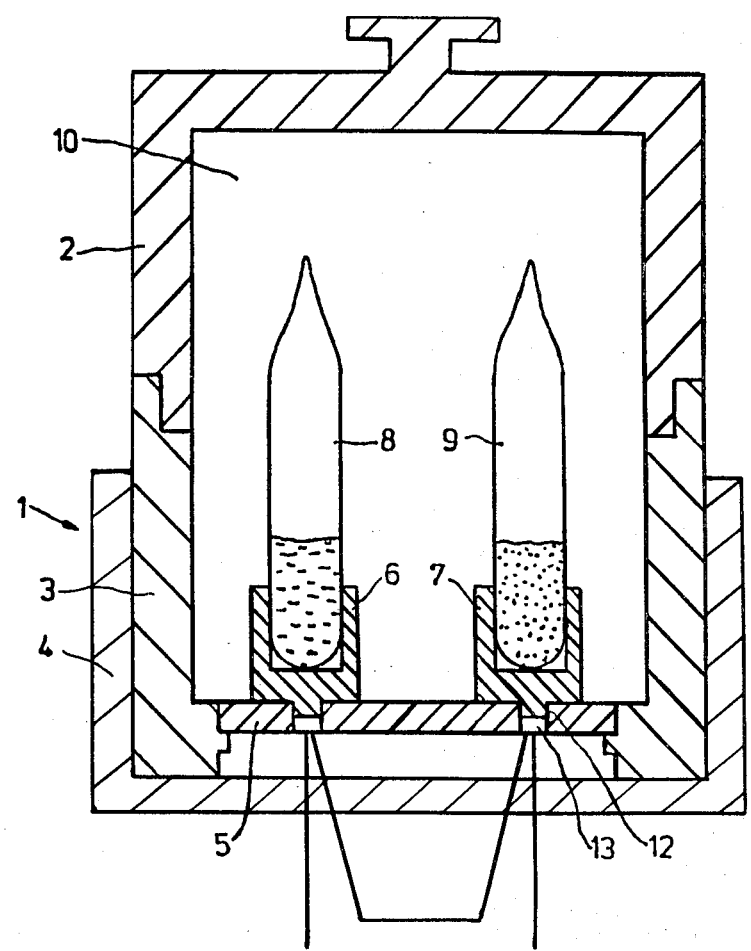
Figure 1A:
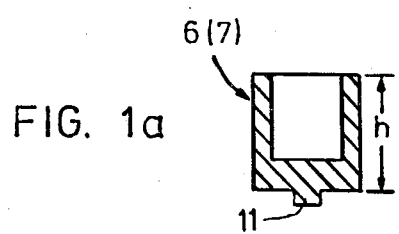

United States Patent [19]

Hentze

[11] 4,368,991

[45] Jan. 18, 1983

[54] APPARATUS FOR DIFFERENTIAL THERMAL ANALYSIS

[75] Inventor: Gunter Hentze, Carl Leverkus-Str. 4, 5068 Odenthal, Fed. Rep. of Germany, D 5068

[73] Assignee: Gunter Hentze, Odenthal, Fed. Rep. of Germany

[21] Appl. No.: 229,875

[22] Filed: Jan. 30, 1981

[30] Foreign Application Priority Data

Feb. 9, 1980 [DE] Fed. Rep. of Germany ....... 3004810

[51] Int. Cl.³ ...................... G01K 17/00; G01N 25/00
[52] U.S. Cl. ...................................................... 374/12
[58] Field of Search ........................................ 73/15 B

[56] References Cited

U.S. PATENT DOCUMENTS

| | | | |
|---|---|---|---|
| 3,283,560 | 11/1966 | Harden et al. | 73/15 |
| 3,285,053 | 11/1966 | Mazieres | 73/15 |
| 3,417,604 | 12/1968 | Bean | 73/15 |
| 3,545,253 | 12/1970 | Iwata et al. | 73/15 |
| 4,095,453 | 6/1978 | Woo | 73/15 |

OTHER PUBLICATIONS

Horlin, et al., Chem. Commun, Univ. Stockholm, 1975 Nr. 9 (Oct. 9).

Primary Examiner—Herbert Goldstein

[57] ABSTRACT

The invention relates to an apparatus for differential thermal analysis, consisting of a furnace with holders to receive vessels sealed on all sides for samples and reference substances and with temperature sensors, which are in good thermal contact with the vessels, characterized in that the holders consist of a metal cylinder open on one side, whose inner diameter is adjusted to the outer diameter of the vessels, and whose bottom is in good thermal contact via a base plate with the furnace, and sensors arranged on the base plate in the immediate vicinity of the cylinder bottom.

3 Claims, 5 Drawing Figures

APPARATUS FOR DIFFERENTIAL THERMAL ANALYSIS

The invention relates to an apparatus for differential thermal analysis, consisting of a furnace with holders to receive vessels for samples and reference substances and temperature sensors, which are in good thermal contact with the vessels.

Measurements of heat of transformation are mostly carried out with the help of differential thermal analysis in open or sealed metal vessels. This has the disadvantage, especially in testing reaction- und decomposition processes, that very frequently catalytic actions that may occur, e.g. of metals of the sample vessel, cannot be recognized. This, however, is very important, because by the eventual catalytic action of the sample container material, a possible catalytic action of catalysts or of the vessel material, in which the reaction is to be carried out later, is masked.

For this reason it is more informative, to measure the heat of transformation in an inert environment, e.g. in a glass container or in a glass or quartz ampul. The measurement in sealed vessels has the advantage, that the heat of evaporation, which overlaps or completely covers other heats of transformation, can not be coincidentally measured. If, for example, an unknown heat of decomposition is measured in an open vessel, then this is overlapped by the unknown heat of evaporation of the "cracked" products. Only in sealed test vessels is it possible to detect the heat of decomposition alone, because hereby the heat of evaporation of the "cracked" products is not detected.

The following procedure is to be used, for example, if the influence of catalysts on a reaction or the influence of the vessel material on a reaction and/or decomposition is to be measured. During a first measurement the heat of transformation of a product mixture in its delivered state is measured. In a second measurement the product or the product mixture is mixed with a catalyst, or the wall material of the vessel is added. If the test curves of the first and second measurement are the same, then the addition of the catalyst and/or the wall material has no influence on thermal behavior (reaction of decomposition) of the substance. If the curves vary, then the influence of the catalyst on the reaction and/or the decomposition or an eventual reaction of the substance with the container wall can be detected.

An apparatus for carrying out differential thermal analyses is described in German OS No. 23 18 340, which is based on a measurement in sealed glass vessels (glass ampuls). The DTA furnace here consists of an electrically heated block, which contains recesses to hold the glass ampuls. The glass ampuls on their bottom are provided with a metal layer or a metal sleeve, in order to guarantee a good thermal contact between the ampul and the temperature sensors. The thermal elements (sensors) for this purpose are welded or soldered directly to the layer or the sleeve. The heating required for the test procedure takes place from the furnace unit via a part of the ampul coating surface. In contrast to this the heat transfer from the bottom (front of the glass ampul) is almost completely stopped.

Such sensors have basically been successfully used to test the thermal behavior of substances in sealed systems. But, in successive tests of substances, i.e. during routine operation, cumbersome handling while changing disturbs the samples. Also, the thermal relationships based on the non-defined contact surface between the glass ampul and the furnace unit are not reproducible under unfavorable conditions.

It is thus the task underlying the invention to show a DTA sensor for testing substances in sealed systems, which meets the high demands of routine operations and offers at least the same security of measurement.

This task is solved by the initially described sensor thereby, that the holders for the vessels (samples and reference substances) consist of a metal cylinder open on one side, whose bottom via a base plate is in good thermal contact with the furnace and the sensor is placed in the immediate vicinity of the cylinder bottom. Advantageously the metal cylinders on their base are provided with pegs or grooves for centering the metal cylinder on the base plate. An essential improvement, moreover, consists therein, that the vessels, except for the part extending into the metal cylinder, are placed free standing in the heater chamber. Appropriately, the vessels are designed for holding material volumes of 20 to 100 mm$^3$.

The handling of the sensors is essentially made easier by these measures. During an exchange of the samples only the fused glass ampul with the substance contained therein is placed with its bottom into the pot-like metal cylinder and is placed on the base plate in the furnace. The peg on the bottom of the metal cylinder (and/or a groove), which fits into a corresponding clearance in the base plate, assures a reproducible set up of the glass ampuls in the furnace. The heat transfer to the sample and/or to the substance during heating no longer takes place as before by direct heat transfer via the metal surfaces of the glass ampuls, but from the bottom via the base plate and by convection in the area of the free standing part of the glass ampuls.

By this mechanism, unobjectionable physical conditions are created for heat transfer. Moreover, an important advantage of the invention is, that no special construction of the furnace is required. Commercially available DTA furnaces have to be only slightly modified so that they become compatible with the apparatus of the invention. This means, that in actual practice, sensors already available for thermal analysis in open vessels can also be used without the problems and expensive rebuilding that would otherwise be necessary.

The invention will now be explained based on embodiments, which are represented in the drawing.

FIGS. 1, 1a, 2, 2a and 3 show schematically different embodiments of DTA sensors for testing substances in sealed glass ampuls.

The sensor according to FIG. 1 consists of a cylindrical DTA furnace 1, which is divided into two halves, i.e., a hood 2 and a bottom part 3. An electrical heater 4 is located on the lower part 3. Cylindrical metal vessels 6 and 7 are located on the bottom 5 of lower part 3 for holding glass ampuls 8 and 9. In the left ampul 8 is placed, e.g., the sample, and in the right ampul 9 an inert substance as a reference material. Ampuls 8 and 9 are inserted up to about one-third of their length into metal cylinders 6 and 7 and, therefore, are in good thermal contact in this area with the metal cylinders. In the remaining part, ampuls 8 and 9 are placed free standing in furnace chamber 10. Metal cylinders 6 and 7 on their bottom have a short peg 11 (see FIG. 1a), which fits into a corresponding recess 12 in the base plate. In this way, metal cylinders 6 and 7 can be reproducibly centered in furnace chamber 10. Thermal elements 13 used as temperature sensors are also placed in recesses 12.

Thus, they are in a very good thermal contact with the base plate 5 as well as with the metal cylinders. Metal parts 2, 3, 5, 6, and 7 are all made of a material of high thermal conductivity, e.g., copper or silver. For measurement, hood 2 is removed and the glass ampuls in their holders 6 and 7 filled with the substance are placed in recess 12 of the base plate. The test procedure can begin immediately after closing hood 2.

Figure 2:
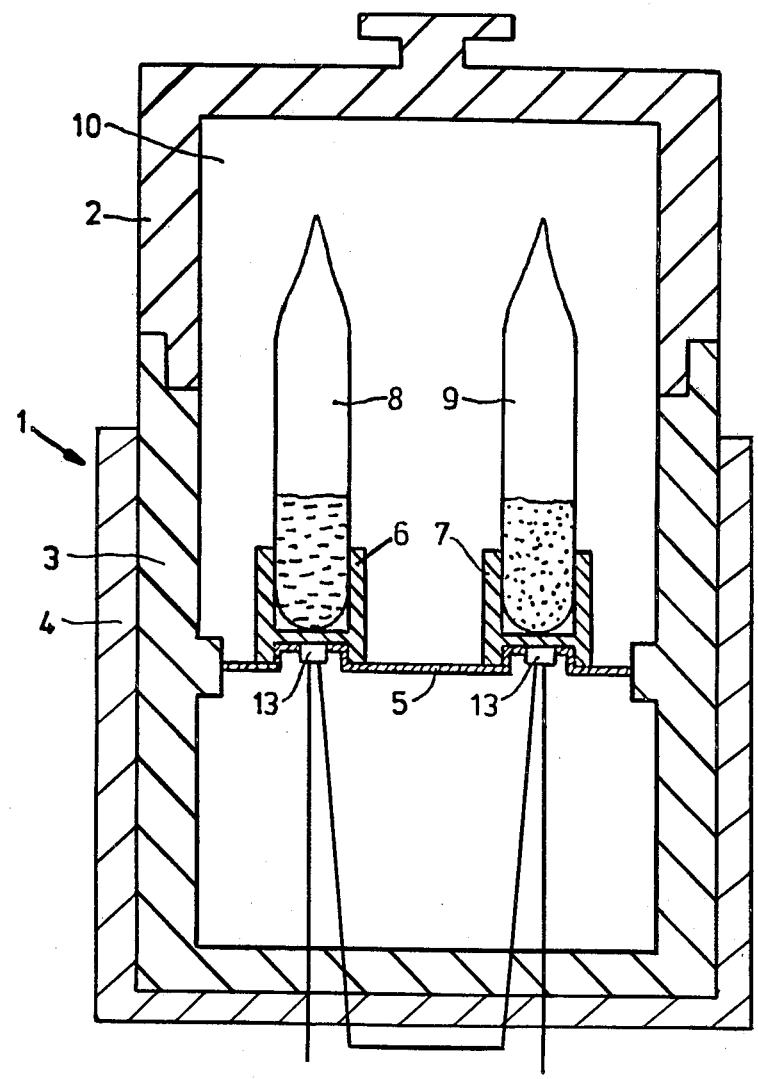
Figure 2A:
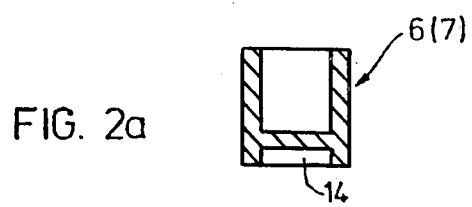

The sensor according to FIG. 2 is designed according to the same principle as in FIG. 1. Base plate 5 here, however, consists of a constantan plate. Thermal elements 13, as in the embodiment according to FIG. 1, are in very good thermal contact with the base plate 5 and the metal cylinders 6 and 7, and in this case are formed by a copper wire welded to base plate 5. Constantan plate 5 is provided with two elevations, which correspond to a groove 14 in the two metal cylinders 6 and 7. Groove 17 (see FIG. 2a) thus in theory has the same function as pegs 11 in FIG. 1a.

Figure 3:
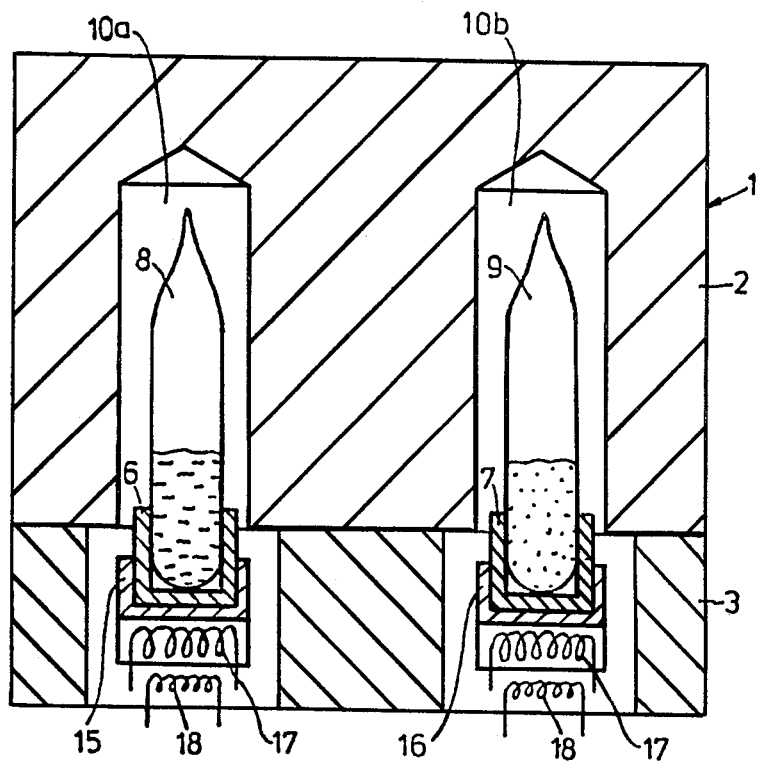

A further embodiment of this sensor is shown in FIG. 3. Ampuls 8 and 9 with their cylindrical holders 6 and 7 here stand in recesses 15 and 16 in the insulating block. Recesses 15 and 16, whose inner diameter corresponds to the outer diameter of metal cylinders 6 and 7, maintain good thermal contact with the substances in the ampuls 8 and 9. Immediately below recesses 15 and 16 for receiving holders 6 and 7 there are heating coils 17, which are in thermal contact with temperature sensors 18 (here resistance thermometers). The furnace hollow chamber here consists of two separate cylindrical chambers 10a and 10b in contrast to the apparatus according to FIGS. 1 and 2. Ampuls 8 and 9, however, are nowhere in contact with the inner wall of chambers 10a and 10b. The arrangement according to FIG. 3 is suited for calorimetric measurements.

In order that the substances measured into ampuls 8 and 9 still exhibit well-measurable heat contents and the mixtures of two reaction components of different consistency can still be produced in the ratio of 1:10, the ampules should be able to hold quantities of ca 30 mg to 100 mg, corresponding to a volume from 20 to 100 mm$^3$. Thus, e.g., ampuls of quartz with a 4 mm inner diameter and an outer diameter of 6.6 mm are usable up to temperatures of 800° C. and pressures of up to 300 bar.

I claim:

1. Apparatus for differential thermal analysis, consisting of a furnace with holders to receive vessels sealed on all sides for samples and reference substances and with temperature sensors, which are in good thermal contact with the vessels, characterized in that the holders consist of a metal cylinder open on one side, whose inner diameter is adjusted to the outer diameter of the vessels, and whose bottom is in good thermal contact via a base plate with the furnace and is provided with pegs or grooves for centering on the base plate and sensors arranged on the base plate in the immediate vicinity of the cylinder bottom.

2. Apparatus according to claim 1, characterized in that the vessels, except for the part placed in the metal cylinders, are arranged free standing in the furnace chamber.

3. Apparatus according to claim 1, characterized in that the vessels are designed for material volumes of 20 to 100 mm$^3$.

* * * * *